(12) United States Patent
Watson et al.

(10) Patent No.: US 6,722,624 B1
(45) Date of Patent: Apr. 20, 2004

(54) TAP

(75) Inventors: Jeremy Watson, Merseyside (GB); Richard John Hunter, Huddersfield (GB)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/926,294

(22) PCT Filed: Apr. 5, 2000

(86) PCT No.: PCT/GB00/01286

§ 371 (c)(1),
(2), (4) Date: Oct. 9, 2001

(87) PCT Pub. No.: WO00/59416

PCT Pub. Date: Oct. 12, 2000

(30) Foreign Application Priority Data

Apr. 6, 1999 (GB) .............................................. 9907832

(51) Int. Cl.⁷ .............................................. F16K 31/44
(52) U.S. Cl. ......................................................... 251/78
(58) Field of Search ...................................... 251/77, 78

(56) References Cited

U.S. PATENT DOCUMENTS

| | | | | |
|---|---|---|---|---|
| 4,540,156 A | * | 9/1985 | Cross | 251/309 |
| 5,076,540 A | | 12/1991 | Murphy | 251/175 |
| 5,496,010 A | * | 3/1996 | Collyer | 251/78 |

FOREIGN PATENT DOCUMENTS

| | | |
|---|---|---|
| EP | 0 428 331 | 5/1991 |
| GB | 2 093 164 | 8/1982 |
| GB | 2 166 222 | 4/1986 |
| HU | 198 238 | 8/1989 |
| HU | 198 150 | 9/1990 |
| WO | 91/03217 | 3/1991 |

* cited by examiner

Primary Examiner—Edward K. Look
Assistant Examiner—John K. Fristoe, Jr.
(74) Attorney, Agent, or Firm—Jacobson Holman PLLC

(57) ABSTRACT

A tap for a urine drainage system, having a body, a lever and a barrel with a through bore which is mounted in the body for rotation between a position for through flow of liquid and a position which obturates fluid flow. The lever is mounted directly on the body for reversible rotation therearound, the arrangement being such that, on rotation of the lever, the barrel is movable between the two positions.

20 Claims, 3 Drawing Sheets

TAP

This is a nationalization of PCT/GB00/01286 filed Apr. 2, 2000 and published in English.

BACKGROUND OF THE INVENTION

1. Field of the Invention

The invention relates to a tap, particularly to a tap for a urine drainage system.

2. Description of the Related Art

Such systems often utilise a catheter for drainage of urine from a patient's bladder into a urine collection bag. Such bags require to be drained periodically, for which purpose where is usually a tap on an outlet tube. The tap is operated by the patient, nurse, or carer. The taps need to be effective in operation even for those with limited dexterity, with no leakage, to avoid soiling and possible cross-contamination, light and with the ability to avoid snagging on clothing or bed clothes.

Such taps often include a lever, but this can be separated from the system under repeated usage, which leads to failure and leakage.

It is accordingly an object of the invention to seek to mitigate this disadvantage.

SUMMARY OF THE INVENTION

According to a first aspect of the invention, there is provided a tap for a urine drainage system, comprising a body and a barrel with a through bore which is mounted in the body for rotation between a position for through flow of liquid and a position which obturates fluid flow, characterised by a lever (4) which is mounted on the body (1) for reversible rotation therearound, the arrangement being that on such rotation the barrel (2) is movable between said two positions.

According to a second aspect of the invention there is provided a urine drainage system including a tap as hereinbefore defined.

The lever and body may be snap-engaged, preferably by the lever having a peripheral flange and the barrel a circumferential groove in which the flange is snap-engaged.

There may be a lost motion connection between the lever and barrel whereby the lever can lie substantially alongside a tube of the system in each of two end, rotated positions, the lost-motion connection preferably comprising a projection from the lever received in a circumferentially longer gap in a facing end of the barrel.

Suitably there may be two spaced projections each received in a respective gap, which gaps and projections may be diametrically opposed, for a balanced operation.

The lever may have an angled free end for gripping by a user, which free end may comprise a bar mounted asymmetrically with respect to the lever.

The component parts may comprise of polypropylene or other polymeric materials and the body may have a blind cylinder in which the barrel is mounted for rotation.

A tap for a urine drainage systems embodying the invention is hereinafter described, by way of example with reference to the accompanying drawings.

BRIEF DESCRIPTION OF THE PREFERRED EMBODIMENTS

Figure 1:
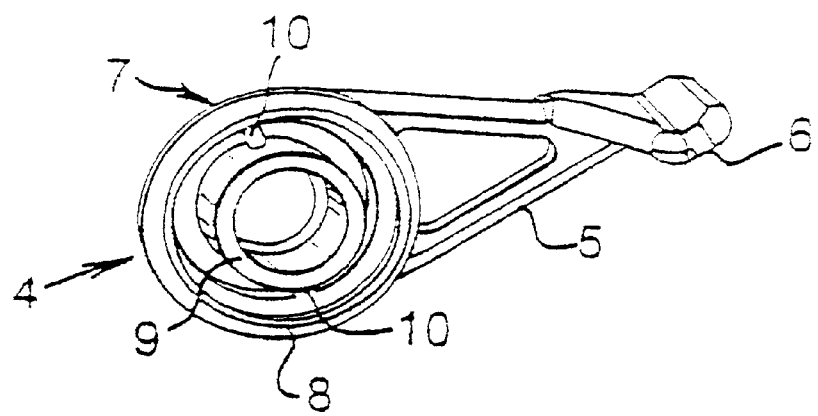
FIG. 1 is a perspective view of the inner side, in use, of a lever of a tap according to the invention.
Figure 2:
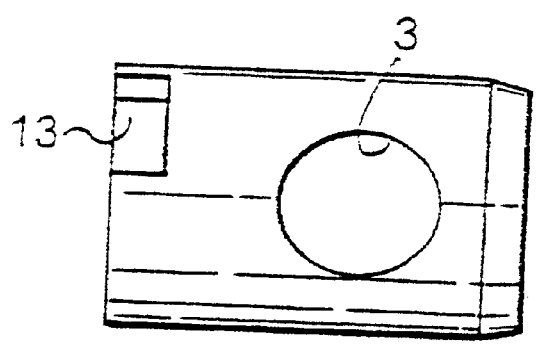
FIGS. 2 to 4 are respective elevational, end views and transverse sectional views of a barrel of the tap.
Figure 3:
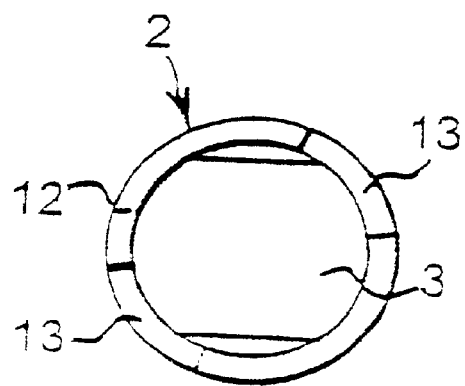
Figure 4:
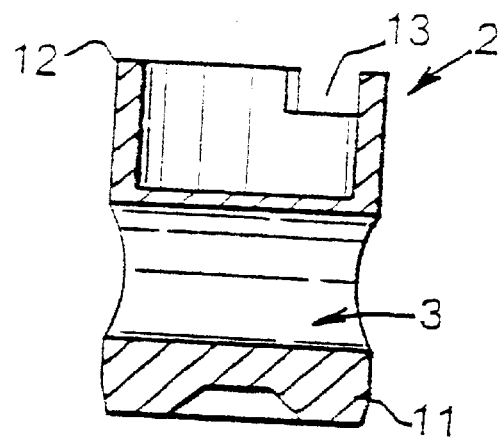
Figure 5:
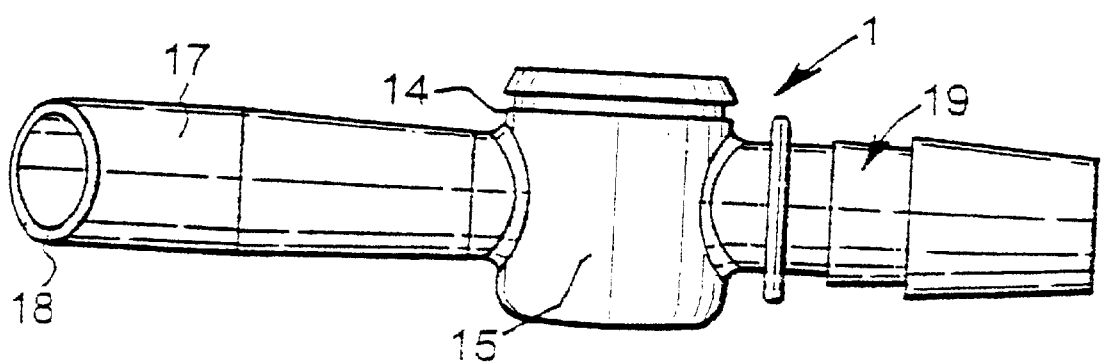
FIGS. 5 to 7 are respective plan, side elevational and longitudinal sectional views of a body of the tap.
Figure 6:
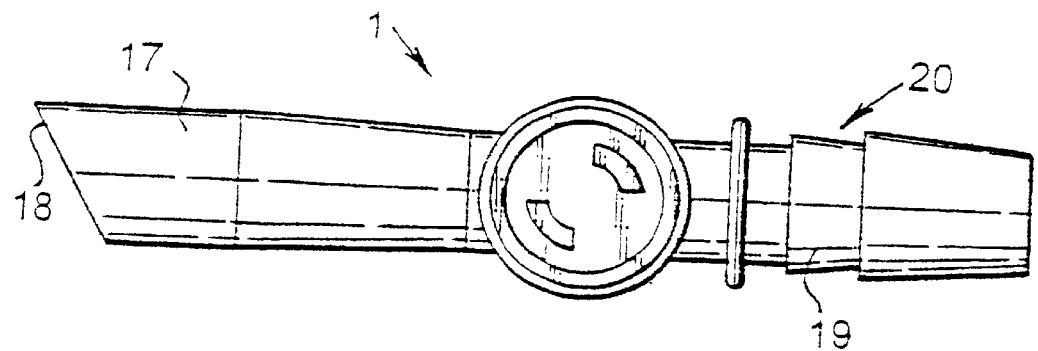
Figure 7:
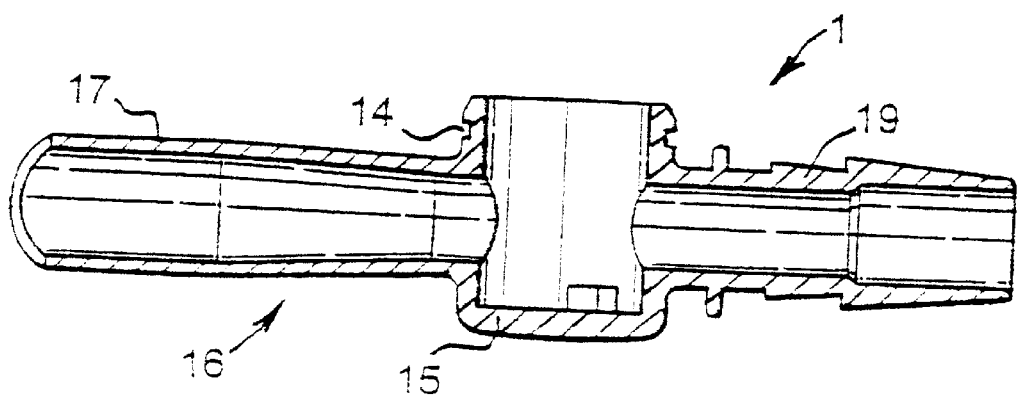

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Referring to the drawings, there is shown a tap for a urine drainage system, comprising a body 1, a barrel 2 with a through bore 3 which is mounted for rotation between a position for through flow of liquid and a position which obturates fluid flow, and a lever 4 which is mounted on the body 1 for rotation therearound to move the barrel 2 between said two positions.

The body 1, barrel 2 and lever 4 comprise parts of the tap, and each is made as a separate, integral, unit or member from a polymeric material such as polypropylene in the embodiment.

The lever 4 has an arm with a free end with an asymmetrical bar 6 for grasping by a user. The other end of the lever 4 has a disc-shaped generally circular part 7 with an upstanding wall carrying a peripheral radially inwardly turned flange 8, an inner cylindrical part 9 and therebetween on a wall defining the part 9, two diametrically spaced projections, dogs or teeth 10, which are lower in height than the cylindrical part 9 and the part 7. There is a gap between a free end of each projection, dog or tooth 10 and the upstanding wall of the part 7, which wall and part 9 are spaced apart radially to receive the projections, dogs or teeth 10. The barrel 2 has the through bore 3 and is generally cylindrical with a blind end 11, the opposite open end having a wall 12 having two diametrically opposed cut-outs, gaps or notches 13 which each have a circumferential length greater than the thickness of the dogs, projections, or teeth 10 on the lever.

The through bore 3 is closed off at a side facing the open side by a cap supported by wings, this arrangement preventing flow of fluid from passing towards the open end.

The body 1 is a blind cylindrical member 15 with a part having a peripheral external groove 14.

There is an integral tube 16 projecting on either side of the member 15, forming an integral body member, part 17 of the tube having a cut away drainage outlet 18, and part 19 a toothed or barbed connector 20 for receiving an outlet tube from a urine drainage bag.

The tap is assembled by mounting the barrel 2 in the body 1, and snap engaging the lever 4 on the body 1 by snap engagement of the flange 8 in the groove 14 the projections, dogs or teeth 10 each being received in a respective gap 13.

When the lever 4 is rotated round the body 1, the groove 14 acting as a guide for the flange 8, the dogs 10 move along the gaps 13 until they strike a wall defining the blind gap, and rotate the barrel 2 to either open or obturate the flow path for liquid from the bag by aligning the bore 3 with the tube 16, or turning it at 90° thereto. Rotational movement of the tap in the opposite or reverse direction obturates or opens the fluid flow.

The gaps 13 and dogs 10 provide a lost motion connection so that the lever lies 4 alongside the tube 16 in each end position, the longer part 5 of the bar 6 of the lever lying over the tube 16 so as to be stowed away from possible snagging on clothing or bed clothing.

Mounting of the lever 4 on the body 1 provides a positive mounting which is separate from the barrel 2 so making it difficult for the lever 4 to be snapped off, and providing essentially a separate connection with the barrel. Thus, as the lever 4 is mounted on the body 1, the pressure on the lever 4 does not bear on the barrel, which is operated solely by the lost motion connection of the dogs 10 in the gaps 13.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A tap for a urine drainage system, comprising a body, a lever, and a barrel with a through bore which is mounted in the body for rotation between a position for through flow of liquid and a position which obturates fluid flow, said lever being mounted directly to the body for reversible rotation therearound, such that, upon said lever rotation, the barrel is moved between said two positions.

2. A tap as defined in claim 1, wherein the lever and the body are snap-engaged.

3. A tap as defined in claim 2, wherein there is a peripheral flange carried by the lever and wherein there is a circumferential groove carried by the body, said groove and flange being snap-engaged.

4. A tap as defined in claim 1, wherein there is a lost motion connection between the lever and the barrel, whereby the lever can lie substantially alongside a tube of the system in each of the two rotated positions.

5. A tap as defined in claim 4, wherein the lost motion connection comprises a projections from the lever received in a circumferentially longer gap in a facing end of the barrel.

6. A tap as defined in claim 4, wherein the lost motion connection comprises two spaced projections projecting from the lever, each of said projections being received in a respective gap in a facing end of the barrel.

7. A tap as defined in claim 6, wherein the gaps and projections are diametrically opposed.

8. A tap as defined in claim 1, wherein the lever has an angled free end for gripping by a user.

9. A tap as defined in claim 8, wherein the angled free end comprises a bar mounted asymmetrically with respect to the lever.

10. A tap as defined in claim 1, wherein the component parts comprise polymeric material.

11. A tap as defined in claim 1, wherein the body has a blind cylinder in which the barrel is mounted for rotation.

12. A tap as defined in claim 1, in combination with a urine drainage system.

13. The tap as set forth in claim 1, wherein the mounting of said lever to said body constrains said barrel within said body, said lever being supported upon said body and engaging a periphery of said barrel.

14. A tap for a urine drainage system, comprising a body, a lever, and a barrel with a through bore which is mounted in the body for rotation between a position for through flow of liquid and a position which obturates fluid flow, said lever being mounted over said barrel and directly to said body for reversible rotation therearound, said lever engaging a peripheral portion of said barrel such that, upon said lever rotation, said barrel is moved between said two positions while pressure on said lever bears upon said body.

15. A tap for a urine drainage system, comprising a body, a lever, and a barrel with a through bore which is mounted in the body for rotation between a position for through flow of liquid and a position which obstructs fluid flow, said lever being snap-engaged to the body for reversible rotation therearound such that, upon said lever rotation, the barrel is moved between said two positions.

16. A tap as defined in claim 15, wherein there is a peripheral flange carried by the lever and wherein there is a circumferential groove carried by the body, said groove and flange being snap-engaged.

17. A tap as defined in claim 15, wherein there is a lost motion connection between the lever and the barrel, whereby the lever can lie substantially alongside a tube of the system in each of the two rotated positions.

18. A tap as defined in claim 17, wherein the lost motion connection comprises a projection from the lever received in a circumferentially longer gap in a facing end of the barrel.

19. A tap as defined in claim 17, wherein the lost motion connection comprises two spaced projections projecting from the lever, each of said projections being received in a respective gap in a facing end of the barrel.

20. A tap as defined in claim 15, wherein the lever has an angled free end including a bar mounted asymmetrically with respect to the lever for gripping by a user.

* * * * *